(12) United States Patent
Agichtein et al.

(10) Patent No.: US 10,694,942 B2
(45) Date of Patent: Jun. 30, 2020

(54) INTERNET-BASED COGNITIVE DIAGNOSTICS USING VISUAL PAIRED COMPARISON TASK

(71) Applicant: EMORY UNIVERSITY, Atlanta, GA (US)

(72) Inventors: Yevgeny E. Agichtein, Atlanta, GA (US); Elizabeth A. Buffalo, Atlanta, GA (US); Dmitry Lagun, Atlanta, GA (US); Cecelia Manzanares, Atlanta, GA (US); Stuart Zola, Atlanta, GA (US)

(73) Assignee: EMORY UNIVERSITY, Atlanta, GA (US)

( * ) Notice: Subject to any disclaimer, the term of this patent is extended or adjusted under 35 U.S.C. 154(b) by 568 days.

(21) Appl. No.: 15/452,521

(22) Filed: Mar. 7, 2017

(65) Prior Publication Data

US 2017/0273555 A1 Sep. 28, 2017

Related U.S. Application Data

(63) Continuation of application No. 13/256,789, filed as application No. PCT/US2010/025489 on Feb. 26, 2010, now Pat. No. 9,629,543.

(60) Provisional application No. 61/299,419, filed on Jan. 29, 2010, provisional application No. 61/160,928, filed on Mar. 17, 2009.

(51) Int. Cl.
*A61B 5/00* (2006.01)
*A61B 3/113* (2006.01)
*A61B 5/16* (2006.01)

(52) U.S. Cl.
CPC ............ *A61B 3/113* (2013.01); *A61B 5/165* (2013.01); *A61B 5/168* (2013.01)

(58) Field of Classification Search
CPC ........... A61B 5/16; A61B 5/162; A61B 5/163; A61B 5/165; A61B 5/168; A61B 5/4064; A61B 5/4082; A61B 5/4088; A61B 3/113
See application file for complete search history.

(56) References Cited

U.S. PATENT DOCUMENTS

| | | | |
|---|---|---|---|
| 6,290,357 B1 * | 9/2001 | Massengill | ............ A61B 3/024 351/209 |
| 6,632,174 B1 | 10/2003 | Breznitz | |
| 7,294,107 B2 | 11/2007 | Simon et al. | |
| 7,403,814 B2 | 7/2008 | Cox et al. | |
| 8,016,416 B1 * | 9/2011 | Straus | .................. A61B 5/1171 351/200 |
| 8,951,046 B2 | 2/2015 | Stack | |
| 2004/0151218 A1 | 8/2004 | Branzoi et al. | |
| 2005/0114177 A1 | 5/2005 | Sweeney | |

(Continued)

OTHER PUBLICATIONS

U.S. Appl. No. 13/256,789, "Non-Final Office Action", dated Aug. 23, 2016, 21 pages.

(Continued)

*Primary Examiner* — Max F Hindenburg
(74) *Attorney, Agent, or Firm* — Kilpatrick Townsend & Stockton LLP (57) ABSTRACT

Disclosed are methods for diagnosing declarative memory loss using mouse tracking to follow the visual gaze of a subject taking a visual paired comparison test. Also disclosed are methods for diagnosing dementia such as mild cognitive impairment and Alzheimer's disease.

18 Claims, 2 Drawing Sheets

(56) References Cited

U.S. PATENT DOCUMENTS

| | | |
|---|---|---|
| 2006/0270945 A1 | 11/2006 | Ghajar |
| 2007/0297641 A1 | 12/2007 | Criddle et al. |
| 2009/0155754 A1 | 6/2009 | Shankle et al. |
| 2009/0298025 A1 | 12/2009 | Raber et al. |
| 2010/0092929 A1 | 4/2010 | Hallowell et al. |
| 2010/0100001 A1 | 4/2010 | Aguilar et al. |
| 2010/0208205 A1 | 8/2010 | Tseng et al. |
| 2013/0090562 A1 | 4/2013 | Ryan |

OTHER PUBLICATIONS

U.S. Appl. No. 13/256,789, "Notice of Allowance", dated Jan. 19, 2017, 10 pages.

U.S. Appl. No. 13/256,789, "Restriction Requirement", dated May 25, 2016, 8 pages.

Chen et al., (2001), "What can a mouse cursor tell us more?: correlation of eye/mouse movements on web browsing", CHI '01 extended abstracts on Human factors in computing systems, Seattle, Washington, ACM: 281-282.

Crutcher et al., "Eye Tracking During a Visual Paired Comparison Task as a Predictor of Early Dimentia", Am J Alzheimers Dis Other Demen. vol. 24, No. 3, 2009, pp. 258-266.

\* cited by examiner

INTERNET-BASED COGNITIVE DIAGNOSTICS USING VISUAL PAIRED COMPARISON TASK

This application is a continuation of U.S. application Ser. No. 13/256,789, filed Nov. 4, 2011, which claims the benefit of U.S. Provisional Application No. 61/160,928, filed on Mar. 17, 2009, and U.S. Provisional Application No. 61/299,419, filed on Jan. 29, 2010 which are incorporated by reference herein in their entirety.

STATEMENT REGARDING FEDERALLY FUNDED RESEARCH

This invention was made with government support under Grant No. EB014266 awarded by the National Institutes of Health. The government has certain rights in the invention.

I. BACKGROUND

The diagnosis of mild cognitive impairment (MCI) refers to individuals who have memory loss but relatively preserved abilities in other cognitive areas (Petersen R C et al. Arch Neurol. 1999 March; 56(3):303-8). Unfortunately, this population appears to be at high risk for developing dementia, especially Alzheimer's Disease (AD) (Morris J C. Geriatrics. 2005 June; Suppl:9-14). The progression rate from MCI to AD is between 6-25% per year (Petersen R C, et al. Neurology. 2001 May 8; 56(9):1133-42). Accordingly, patients with MCI are an important target for the development of research strategies that will lead to early diagnosis and possible prevention of dementia (Burns A, Zaudig M. *Lancet*. 2002 Dec. 14; 360(9349):1963-5).

II. SUMMARY

Disclosed herein, in one aspect, are methods related to the identification of patients with Mild Cognitive Impairment (MCI) and the diagnosis of Alzheimer's Disease (AD).

III. BRIEF DESCRIPTION OF THE DRAWINGS

The accompanying drawings, which are incorporated in and constitute a part of this specification, illustrate several embodiments and together with the description illustrate the disclosed compositions and methods.

IV. DETAILED DESCRIPTION

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

The memory impairment associated with MCI has been linked to structural changes beginning in the medial temporal lobe (Braak H, Braak E. *Acta Neuropathol (Berl)*. 1991; 82(4):239-59; Braak H, Braak E. Neurobiol Aging. 1997 July-August; 18(4 Suppl):S85-8). In particular, structures in the medial temporal lobe, including the hippocampal region, together with the entorhinal, perirhinal, and parahippocampal cortices have been found to make up what is now referred to as the medial temporal lobe memory system. Damage to components of this system produce impairments in declarative memory, i.e. the ability to consciously recollect facts and events (Eichenbaum H. Behav Brain Res. 2001 Dec. 14; 127(1-2):199-207; Squire L R, Zola-Morgan S. Science. 1991 Sep. 20; 253(5026):1380-6). These impairments in declarative memory give rise to the hallmark memory complaints made by Alzheimer's Disease (AD) patients and observed by their family members. However, given the lengthy prodromal phase of AD, which can last up to 7 to 10 years (Elias M F, et al. Arch Neurol. 2000 June; 57(6):808-13; Linn R T, et al. Arch Neurol. 1995 May; 52(5):485-90), many of the early memory changes that take place can go undetected until well into the course of the disease. Therefore, it is critical to have available very sensitive memory tests in order to detect memory deficits as early in the disease process as possible.

Disclosed herein are methods of diagnosing a subject with declarative memory loss. It is understood that declarative memory loss can be caused by many factors including but not limited to damage to the medial temporal lobe of the brain. In particular, such damage can be located in the hippocampal region of the medial temporal lobe. Thus, in one aspect, disclosed herein are methods of diagnosing a subject with declarative memory loss, wherein the memory loss is caused by damage to the medial temporal lobe. Also disclosed herein are methods of diagnosing a subject with declarative memory loss, wherein damage to the medial temporal lobe is located in the hippocampal region.

It is understood and herein contemplated that there are many ways that a subject can be diagnosed with declarative memory loss, mild cognitive impairment, or AD. However, until the present disclosure such methods would require a battery of tests assessing cognitive and physiological changes. A critical goal of Alzheimer's disease research is to improve current methods of diagnosis so that patients can be identified sooner and, therefore, obtain greater advantage from available therapies. Disclosed herein are methods of diagnosing a subject with declarative memory loss, mild cognitive impairment, and/or AD comprising administering to the subject a VPC task.

The VPC task is a recognition memory task that assesses the proportion of time an individual spends viewing a new picture compared to a picture they have previously seen, i.e. novelty preference. An important characteristic of normal individuals is that they tend to focus disproportionately more attention on those aspects of the environment that are the most novel (Berlyne D E. Conflict, arousal, and curiosity. New York: McGraw-Hill; 1960; Daffner K R, et al. Neurology. 1992 February; 42(2):320-8; Loftus G R, Mackworth N H. J Exp Psychol Hum Percept Perform. 1978 November; 4(4):565-72). By contrast, patients with Alzheimer's disease spend an equal amount of time looking at the new and repeated pictures, indicating their lack of memory for the repeated pictures.

The VPC task also has many advantages over other memory measures. Unlike many declarative tasks that require extensive training, the VPC task requires little to no instruction. Additionally, the VPC task requires no language comprehension or production, as well as minimal motor output, hence its previous successful use with rodents (Clark R E, et al. J Neurosci. 2000 Dec. 1; 20(23):8853-60), primates (Zola S M, et al. J Neurosci. 2000 Jan. 1; 20(1): 451-63), infants (Fagan J F, 3rd. Ann N Y Acad Sci. 1990; 608:337-57; discussion 58-64) and adults (Manns J R, et al. Proc Natl Acad Sci USA. 2000 Oct. 24; 97(22):12375-9; Richmond J, et al. Dev Psychobiol. 2004 March; 44(2):146-55). Therefore, the VPC task can be used with participants whose verbal and motor skills substantially vary. This is quite beneficial when assessing for cognitive deficits in individuals with varying educational backgrounds and intellectual capabilities.

As shown herein, there is a significant difference between patients with Mild Cognitive Impairment (MCI) and Normal Controls (NC) in overall preference for the novel images. Collecting these kinds of data often requires the use of an eye tracker to precisely monitor subjects' eye movements. Unfortunately, though eye trackers can effectively be used, they are expensive, require trained personnel, and are not widely available. However, the movement of an input device (e.g., a mouse, joystick, touch pad, touchscreen, or trackball) on a computer can correlate with gaze position. By analyzing the computer the position and trajectory of the input device using machine learning techniques, it is often possible to predict the subjects' regions of interest and attention. Moreover, a computer or internet based VPC task can be administered by anyone, even over the internet, without requiring any special purpose hardware, and the associated algorithms for robust analysis and diagnosis of the resulting data. The tools eliminate the need for patients to come to the clinic for initial diagnosis or to participate in research, because they are able to simply log on to a computer and take the cognitive assessment. Thus disclosed herein are methods of diagnosing a subject with declarative memory loss, mild cognitive impairment, and/or AD comprising administering to the subject a VPC task, wherein the eye movement characteristics a subject has on old and novel images is determined by measuring gaze position via an eye tracker or the movement of an input peripheral. For example disclosed herein are methods of diagnosing a subject with AD comprising administering to the subject a VPC task, wherein the looking time is determined by assessing eye movement characteristics as provided by tracking mouse movements on a computer.

In regards to the VPC task, expected normal performance is characterized by more time spent looking at the new picture than the old one. By contrast, memory impaired performance is characterized by looking times that were about equally distributed between the novel and familiar pictures, i.e. impaired declarative memory for what has already been viewed. Thus, disclosed herein are methods of diagnosing a subject with declarative memory loss comprising conducting a visual paired-comparison test wherein a decrease in looking time at the novel image relative to a normal control as determined by eye movement characteristics indicates the presence of declarative memory loss.

It is understood and herein contemplated that looking time can be assessed in numerous ways to determine the relative looking time of the new image. For example, as noted above, the looking time spent by a subject for the new image can be compared to the looking time spent by a normal control for the new image and the times compared, wherein a decrease in the looking time for the novel image indicates the presence of declarative memory loss, MCI, or AD. An equally valid approach is to compare the looking time for a novel image relative to a familiar image. In such a comparison, an approximately equivalent time indicates the presence of declarative memory loss, MCI, or AD whereas a disproportionate time spent on the novel image indicates a normal subject. Thus, disclosed herein are methods of diagnosing a subject with declarative memory loss comprising conducting a visual paired-comparison test utilizing a computational device (such as a computer (e.g., a desktop, notebook, netbook, smartphone, or computational pad), a remote server, or web based utility) and an input device, wherein the delay interval between the familiarization phase and the test phase is at least five seconds, and wherein a looking time that is equivalent for a novel image relative to a familiar image as determined by eye movement characteristics indicates the presence of declarative memory loss.

Alternatively, performance on the VPC task can be analyzed in considerable detail when it is administered in conjunction with the use of non-invasive infrared eye tracking. Eye tracking is the process that can either measure the point of gaze (i.e., where the subject is looking) or the motion of an eye relative to the head. To accomplish this task, a device which measures eye movement and/or eye position is used. Eye trackers can comprise contact mechanisms such as an object which attaches to the eye and allows for measurement or non-contact mechanisms, or electrodes which are placed near the eye and measure electrical potential generated for eye movement. For non-contact mechanisms light, for example infrared light, is reflected from the eye and measured by a video camera or optical sensor. The eye rotation is then determined from the relative measurements. Thus disclosed herein are methods of diagnosing a subject with declarative memory loss, MCI, or AD comprising conducting a visual paired-comparison test wherein looking time is determined by non-invasive eye tracking. Also disclosed are methods wherein the non-invasive eye tracking is conducted through the use of non-invasive infrared eye tracking. It is further understood that eyes can also be tracked by videotaping a subject and scoring videos frame-by-frame for gaze direction. However, this does not yield any additional information such as pupil diameter, or duration of individual fixations. Direct observation can also be used, but does not allow for in depth analysis and relies heavily on tested engagement during the session. Thus, for example, disclosed herein are methods of diagnosing a subject with declarative memory loss comprising conducting a visual paired comparison test wherein the test is administered using non-invasive eye tracking.

It is understood that declarative memory loss from damage to the medial temporal lobe may be indicative of mild cognitive impairment (MCI). Mild cognitive impairment (MCI) is defined as a condition which results in a cognitive decline greater than expected for an individual's age and education level but that does not interfere notably with activities of daily life. Typically, in MCI nerve cells involved in one aspect of cognitive processing (memory) are impaired. Patients with MCI develop a progressive decline in their memory over time. Typically, MCI can be viewed upon as a transition stage between the cognitive decline of normal aging and the more serious problems caused by Alzheimer's disease. The difference between MCI, Alzheimer's disease (AD), and other forms of dementia is the extent of the changes in the brain such as plaques, tangles, hippocampal shrinkage, and lewy bodies, with the changes in MCI often being limited. Prior to the present disclosure, no single test can detect mild cognitive impairment. Instead, the disorder is diagnosed by excluding other conditions that might be causing the signs and symptoms. In order to diagnose an individual with MCI, and ultimately AD, patients are subject to neurological exams, mental status exams, lab tests, and brain scans. Thus, in a further aspect, disclosed herein are methods of diagnosing a subject with mild cognitive impairment. As MCI is often early stage Alzheimer's Disease, disclosed herein, in yet a further aspect, are methods of diagnosing a subject with Alzheimer's Disease (AD).

In three species, rats (Clark R E, et al. J Neurosci. 2000 Dec. 1; 20(23):8853-60) humans (McKee R D, Squire L R. J Exp Psychol Learn Mem Cogn. 1993 March; 19(2):397-404; Manns J R, et al. Proc Natl Acad Sci USA. 2000 Oct. 24; 97(22):12375-9) and monkeys (Bachevalier J et al. Neuroreport. 1993 January; 4(1):77-80; Zola S M, et al. J Neurosci. 2000 Jan. 1; 20(1):451-63) lesions of the hippocampus produce impaired declarative memory and impaired performance on the VPC task. In monkeys, performance on the task was impaired even when 70-80% of the hippocampus was spared (Zola S M, et al. J Neurosci. 2000 Jan. 1; 20(1):451-63). Moreover, monkeys with hippocampal lesions performed relatively worse on the VPC task than on other tests of recognition memory when the same delay intervals were used. Therefore, the VPC task is very sensitive to minimal damage to the hippocampus and is especially useful in diagnosing impaired declarative memory in individuals with little detectable damage to the hippocampus, e.g. patients with MCI who are in the early stages of AD.

To perform the VPC task over the internet or on a computer, an input device is needed to locate the gaze of a subject being assessed or MCI, AD, Parkinson's or other related cognitive impairments. It is understood and herein contemplated that any computer input device that can direct cursor movement is sufficient for the methods disclosed herein. Thus, for example, the input device can comprise a touch pad, a mouse, a trackball, a joystick, a light pen, or pressure on a touch screen. As the subject moves the input device to direct cursor movement on a testing device (e.g., a computer), the movements of the cursor are tracked allowing for the gaze of the subject to be determined.

The delay interval refers to the intentional delay created between the familiarization phase and test phase of a VPC. It is disclosed herein that time of the delay between the familiarization phase and the test phase is critical for the diagnosis of declarative memory loss, MCI, and AD. A time that is too short will not allow sufficient time for memory to be required and therefore unable to create a diagnosis. It is disclosed herein that any delay interval greater than 5 seconds is sufficient for this diagnosis. Thus, for example it is contemplated herein that the delay interval is at least 5 seconds, 6 seconds, 7, seconds, 8, seconds, 9 seconds, 10 seconds, 11 seconds, 12, seconds, 13, seconds, 14 seconds, 15 seconds, 20 seconds, 25 seconds, 30 seconds, 45 seconds (i.e., 0.75 minutes), 1 minute, at least 1.25 minutes, at least 1.5 minutes, at least 1.75 minutes, at least 2 minutes, at least 2.25 minutes, at least 2.5 minutes, at least 2.75 minutes, at least 3 minutes, at least 3.25 minutes, at least 3.5 minutes, at least 3.75 minutes, at least 4 minutes, at least 4.25 minutes, at least 4.5 minutes, at least 4.75 minutes, and at least 5 minutes. It is further understood that delay times greater than 5 minutes will properly diagnose a subject with declarative memory loss, MCI, or AD (for example at least 6 minutes, at least 7 minutes, at least 8 minutes, at least 9 minute, and at least 10 minutes); however, such times can be impractical in application due to the time that the total testing would take. Nevertheless, disclosed herein are methods wherein the delay interval is at least 6 minutes, at least 7 minutes, at least 8 minutes, at least 9 minute, and at least 10 minutes. Specifically disclosed herein are methods of diagnosing a subject with declarative memory loss, MCI, or AD comprising administering to the subject a VPC task, wherein the delay interval between the familiarization phase and the test phase of the test is between 5 seconds and 5 minutes, 5 seconds and 4 minutes, 5 seconds, and 3 minutes, 5 seconds and 2 minutes, 5 seconds and 1 minute, 10 seconds and 5 minutes, 10 seconds and 4 minutes, 10 seconds, and 3 minutes, 10 seconds and 2 minutes, 10 seconds and 1 minute, 30 seconds and 5 minutes, 30 seconds and 4 minutes, 30 seconds and 3 minutes, 30 seconds and 2 minutes, 30 seconds and 1 minute, 1 and 5 minutes, 1 and 4 minutes, 1 and 3 minutes, 1 and 2 minutes, 2 and 5 minutes, 2 and 4 minutes, 2 and 3 minutes, 3 and 5 minutes, 3 and 4 minutes, and 4 and 5 minutes. Thus for example, the delay interval can be 1 minute, 1.5 minutes, 2 minutes. 2.5 minutes, or 3 minutes. Accordingly, disclosed herein are methods of diagnosing a subject with declarative memory loss, wherein the declarative memory loss is caused by damage to the medial temporal lobe. It is understood that the damage to the medial temporal lobe is located in the hippocampal region.

Also disclosed herein are methods of diagnosing a subject with MCI comprising conducting a visual paired-comparison test wherein the delay interval between the familiarization phase and the test phase is at least one minute, and wherein a decrease in looking time at the novel image relative to a normal control as determined by eye movement characteristics indicates the presence of declarative memory loss. Also disclosed are methods of diagnosing a subject with MCI, wherein the MCI is early stage Alzheimer's disease (AD). Also disclosed are methods of diagnosing a subject with MCI or Alzheimer's disease comprising conducting a visual paired-comparison test wherein the delay interval between the familiarization phase and the test phase is at least thirty seconds and wherein a decrease in looking time at the novel image relative to a normal control as determined by eye movement characteristics indicates the presence of MCI or Alzheimer's disease. Also disclosed are methods of diagnosing a subject with MCI or Alzheimer's disease comprising conducting a visual paired-comparison test wherein the delay interval between the familiarization phase and the test phase is at least thirty seconds and wherein a decrease in looking time at the novel image relative to a normal control as determined by eye movement characteristics indicates the presence of MCI or Alzheimer's disease, and wherein the delay interval is 2 minutes.

It is understood that a single VPC task can be administered multiple times to achieve a consensus result for the subject. Thus, a single round would comprise a familiarization phase, a delay interval, and a test phase. Therefore, is understood and herein contemplated that multiple rounds of the VPC test means to run 2, 3, 4, 5, 6, 7, 8, 9, 10, 11, 12, 13, 14, 15, 16, 17, 18, 19, or 20 rounds of the VPC. Alternatively, several successive familiarization round can be employed before multiple testing rounds. For example, a single VPC task can comprise at least one familiarization stage and at least three test stages separated by a delay interval. Therefore, it is contemplated herein that the VPC task can also comprise 1, 2, 3, 4, 5, 6, 7, 8, 9, 10 or more familiarization stages and 3, 4, 5, 6, 7, 8, 9, 10, 11, 12, 13, 14, 15, 16, 17, 18, 19, 20 or more test stages. It is further understood that there can be any combination of the number of familiarization and testing stages, but that the accuracy of the testing increases proportionally with the number of testing stages. However, as with the delay interval, there is practical limit such that a large number of tests can be impractical in application due to the time that the total testing would take.

The time during which the subject is allowed to gaze at the image during the familiarization stage and the test stage is referred to as the "stage time." It is understood and herein contemplated that any stage time between 1 second and 1 minute can be used in the disclosed methods. For example, stage times can be 1, 2, 3, 4, 5, 6, 7, 8, 9, 10, 11, 12, 13, 14, 15, 20, 25, 30, 35, 40, 45, 50, 55, or 60 seconds or any time in between.

Typical VPC task displays two images an old and a new image. When conducted with non-invasive infrared eye tracking the gaze position of the eye is measured with the eye tracker. By contrast, the disclosed internet based cognitive test utilizes optical blurring to disguise an image and allow the user to reveal portions of an image during testing. Blurring of the image can be caused through the use of any device or algorithm to achieve a blurring effect referred to as a Bokeh effect. For example, the blurring can be achieved through the use of a low pass optical filter such as, for example a Gaussian blur, a box blur, lens blur, quartz composer defocus, or butterworth filter. It is understood that any other effect which can result in blurring or pixel smoothing can be used in the disclosed methods. It is further understood that the smoothing effect of the blur can be applied in more than one loop (i.e., cycle). Increasing the number of loops to which the blur is applied creates a larger blur area without sacrificing processing power or time. Thus, for example, disclosed herein are methods of performing an internet or web based cognitive diagnostics using a visual based comparison task comprising blurring an object with a low pass filter, wherein the 1 or more loops of blur are applied. For example, disclosed herein are methods of internet based visual comparison task wherein 2, 3, 4, 5, 6, 7, 8, 9, 10, 11, 12, 13, 14, 15, 20, 24, 30, 35, 40, 45 50, 100, or more loops of blur are applied to the image.

The amount of blurring used is not only affected by the number of loops or cycles of filtering applied to the image but also the pixel radius of the effect. A loop radii applied two times will have the same effective blur size as a blur radii equal to the square root of the sum of the square of the two radii actually run. The skill artisan will more quickly note the representation that radii $C=\sqrt{(A^2+B^2)}$. For example, a first loop with a radii of 3 pixels followed by a second loop with a radii of 4 pixels would have the equivalent blur to a radii of 5 pixels. Thus, for example a radii of 20 pixels applied to 3 loops would have the effective radii of $\sqrt{(20^2+20^2+20^2)}$ or a single blur with a radii of 34.6 pixels. Disclosed herein are methods wherein the radii of the filter for one or more loops of blur is 1, 2, 3, 4, 5, 6, 7, 8, 9, 10, 11, 12, 13, 14, 15, 20, 25, 30, 35, 40, 45, 50, 60, 65, 70, 75, 80, 85, 90, 94, 100, pixels or any number of pixels in between. It is further understood that each successive loop of blur can have the same or different size radii. For example, a blur applied in three loops can be three consecutive loops with a radii of 20 pixels each or alternatively the first second and third radii can be 19, 20, and 21 pixels respectively. It is understood that any combination of radii can be used for each loop of blur applied. It is also understood that if different radii are used in each loop, the order of the radii can be ascending, descending or random.

As the subject is conducting the VPC task, an oculus is moved throughout the image to incrementally reveal the image to the subject. The size of the oculus can be configured to reveal more or less of the image as desired by the administrator of the test. The size of the oculus can be expressed as a percentage of visual angle for the subject or as a dimensional object with pixels as the unit of measure. Thus, for example, the oculus can comprise at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, or 33% visual angle of the visual field subject. Depending on where the subject is seated relative to the testing screen, a given visual angle can comprise more or less pixels. It is understood that the further back the subject is positioned, the smaller the visual angle and thus if a particular visual angle is desired, the number of pixels will increase the further back a subject is positioned to achieve the same visual angle. Thus, for example, disclosed herein are methods of performing a internet based VPC wherein the oculus comprises 5% of the visual angle.

It is understood and herein contemplated that the shape of the oculus can vary depending on the dimensional characteristics of the height and width chosen by the test administrator. Thus, for example, the oculus can be a circle (when both height and width are the same) or oval (when the height and width are not equal). As the height or width changes relative to the other dimension, the oculus appears more ovular. For example, an oculus with 180 pixel width and 120 pixel height is shaped like an oval whereas an oculus with a width and height of 180 pixels is shaped like a circle.

As the height and width dimensions converge, the oculus appears more circular. One of skill in the art understands that depending on the particular filter used and the algorithm used to create the oculus the shape of the oculus can also be squared, rectangular, hexagonal, octagonal, pentagonal, triangular, heptagonal, nonagonal, or decagonal.

Regardless of the shape or size of the oculus, it is understood less than ⅓ of the image can vary at any one time. Thus, disclosed herein are methods of conducting a VPC task wherein the percentage of the image that varies is 33, 32, 31, 30, 29, 28, 27, 26, 25, 24 23, 22, 21, 20, 19, 18, 17, 16, 15, 14, 13, 12, 11, 10, 9, 8, 7, 6, 5, 4, 3, 2 1, 0.75, 0.5, 0.25, or 0.1 percent.

It is understood that because the methods disclosed herein utilize the physical movement of an input device to measure a subjects gaze, motor deficiencies in the subject can create errors in the measurement. For example, a subject with Parkinson's disease, Turret's syndrome, muscle spasms, or other motor related deficiency may have involuntary movements that make tracking gaze of the subject by measuring the movement of the input device difficult. Thus, contemplated herein are methods of diagnosing cognitive impairment using a computer based VPC task further comprising a calibration step to assess any tremors, jerks or other involuntary movements in the subject.

It is also understood that because the oculus size and visual angle are important for the proper calibration and calculation of eye movement characteristics, care must be taken to insure that screen resolution, pop-up windows, alerts (e.g., e-mail, calendar, update, virus, spyware, malware, or program alerts), screen size, or other possible distracting events are minimized. Thus, it is contemplated herein that the computer or internet based VPC task automatically detects screen resolution and size and self-calibrates to compensate for different screen sizes and resolutions to maintain roughly the same visual angle. Such calibration could be achieved either by adjusting the images (e.g., resizing the image and oculus) to compensate or by adjusting the calculations to compensate. Additionally, it is contemplated that the program running the VPC task can operate in full-screen mode and reduce any other program running while the test is administered to the background of the computer or require that other programs close prior to administration of the test. Alternatively, the computer based VPC task can adjust by noting the minimization of the test window or presence of distracting events which could have the effect of loosing mouse focus. The program could then disqualify peripheral input corresponding to the distractors.

Also disclosed are methods of diagnosing a subject with a cognitive disorder comprising conducting a visual paired comparison task on a subject; wherein the task is administered using a visual image examination interface and a peripheral input device; wherein a set of eye movement characteristics are generated through the use of the peripheral input device; and wherein the eye movement characteristics are classified as relating to a particular diagnosis. It is understood and herein contemplated that the administration of the visual based comparison task, and the diagnosis can occur on a computational device or through the use of a remote device (e.g., a remote server) or internet based utility. It is further understood that eye movement characteristics generated correlate to the fixations and looking time of the same subject using an eye tracker. Thus, the a subject with eye movement characteristics that are indicative of an equivalent number of fixations of the familiar image relative to the novel image indicates the subject has a cognitive disorder.

Alternatively, to avoid improper diagnoses due to physical deficiencies in the subject, the disclosed computer based VPC task can be administered in conjunction with mouse tracking, the VPC task can be analyzed using a non-invasive infrared eye tracking. Alternatively, infrared eye tracking can be used as the sole means for conducting the VPC task. Eye tracking is the process that can either measure the point of gaze (i.e., where the subject is looking) or the motion of an eye relative to the head. To accomplish this task, a device which measures eye movement and/or eye position is used. Eye trackers can comprise contact mechanisms such as an object which attaches to the eye and allows for measurement or non-contact mechanisms, or electrodes which are placed near the eye and measure electrical potential generated for eye movement. For non-contact mechanisms light, for example infrared light, is reflected from the eye and measured by a video camera or optical sensor. The eye rotation is then determined from the relative measurements. Thus disclosed herein are methods of diagnosing a subject with declarative memory loss, MCI, or AD comprising conducting a computer based visual paired-comparison test wherein looking time is determined by measuring the movement of an input device (i.e., assessing the eye movement characteristics) and by non-invasive eye tracking. Also disclosed are methods wherein the non-invasive eye tracking is conducted through the use of non-invasive infrared eye tracking. It is further understood that eyes can also be tracked by videotaping a subject and scoring videos frame-by-frame for gaze direction. However, this does not yield any additional information such as pupil diameter, or duration of individual fixations. Direct observation can also be used, but does not allow for in depth analysis and relies heavily on tested engagement during the session.

To facilitate mouse tracking such that the data achieved correlates with eye tracking and can be used to diagnose cognitive disorders, data or "features" from the subject's use of the peripheral input device while using a visual image examination interface are input into one or more classifiers which associate the input data with a one or more groups. These classifications are then "translated" using algorithms to arrive at an endpoint diagnosis. It is understood and herein contemplated that the oculus position is analyzed to estimate eye position during examination and data is collected based on designated points of the oculus such as the oculus center, leading edge and trailing edge.

Gaze position within the oculus can be determined through the use of various models known in the art. For example, a Gaussian model which estimates time spent by subject's gaze being in fixation as two dimensional Gaussian probability density function can be used. An example of such a function is represented by $$f_{gaussian_{gaze}}(x, y) = \frac{1}{2\pi\sigma_x^2\sigma_y^2} e^{-\left(\frac{(x-x_0)^2}{2\sigma_x^2} + \frac{(y-y_0)^2}{2\sigma_y^2}\right)}$$

where variable x and y are orthogonal axis parallel to oculus radiuses. Point $[(x)_0, y_0]$ is center of oculus, $\sigma_x$ equal to one sixth of oculus width and $\sigma_y$ one sixth of oculus height, making probability of gaze position being outside the oculus almost zero. The eye fixation shape is normalized to 5 degrees of visual angle.

Alternatively in conjunction with Gaze position, a leading edge model can be used. The leading edge model is in face modification of Gaussian model, where velocity vector is computed and Gaussian center [(x)$_0$,y$_0$) is biased to the oval border of the oculus, coordinate system of (x,y) is rotated to the parallel and orthogonal directions of the velocity vector.

Similarly the oculus position can be analyzed using a data driven model. This model uses statistically large number of eye movement fixations to estimate mapping (function) of fixation duration to density of gaze position within the fixations.

It is understood that any one or more of these models may be used alone or in combination to produce the as determined by eye movement characteristics (i.e., the data or "features") to produce a diagnosis. It is further understood and herein contemplated that types of data or "features" that may be derived through the use of the peripheral input device which can be used to classify the subject based on the data. Such types of data or features can comprise but are not limited to fixation, saccade, re-fixation, trajectory, and heuristic. While each type of data relates to a particular feature, it is understood that there are many methods to measure or calculate the data.

For example, "fixation" refers to time spent by subject's "gaze" within localized space area (that is fixation area) and in fact they hold local metrics of eye movement scan path. Features in this group represent overall number of fixations and parameters of statistical distribution of fixation duration. Thus, for example, fixation can be determined through the determination of one or more of the following parameters: number of fixations, mean of log (fix duration), standard deviation of the log(fix duration), log(fixDur) distribution fitting parameter (fitted to Inverse Gaussian), Gamma distribution fitting parameter a (log(fixDur)), Gamma distribution fitting parameter b (log(fixDur)), and First maximum in (1/log(fixation duration)) distribution.

Saccade features contain information about saccade shape, time duration of saccade and its size and represent global trajectory characteristic. Saccade can be determined through the determination of one or more of the following parameters: mean of log(saccade duration), standard deviation of log(saccade duration), mean of log(saccade length), standard deviation of log(saccade length), standard deviation of log(saccade segment angle), mean of log(saccade segment angle), mean of saccade following, standard deviation of saccade following, and number of saccades with large (>0.1) following, where $$\text{SaccadeFollowing} = \Sigma_{i=1}^{N} |\alpha_i - \alpha_0|$$

Re-fixation features account for tendency of subject to return to previously seen parts of image and examine them more than one time. Re-fixation can be determined through the determination of one or more of the following parameters: sum of re-fixation duration, number of "deepest" re-fixation divided by total number of fixation, mean of re-fixation depth, and number of peaks in re-fixation sequence.

Trajectory features hold angular trajectory characteristics as well as its space length. That is trajectory refers to the spatial movement (both direction and distance) of the oculus as directed by the peripheral input device. Trajectory can be determined through the determination of one or more of the following parameters: mean of trajectory edge slope, standard deviation of trajectory edge slope, sum of trajectory edge slope, number of trajectory points with big (>0.1) curvature, mean of point-to-point abs (velocity), standard deviation of point-to-point abs (velocity), mean of point-to-point abs (acceleration), standard deviation of point-to-point abs (acceleration), mean of square under saccade, standard deviation of log(square under saccade), mean distribution of log(square under trajectory edge), and maximum of acceleration.

Heuristic type of features serve as auxiliary for rest of the features. This group of features is derived from Fourier transform and statistical distribution properties. Heuristic can be determined through the determination of one or more of the following parameters: mean of inverse DFT from trajectory curvature vector, standard deviation of derivative (inverse DFT distribution of saccade Following), first minimum in derivative of distribution (log(Square under saccade)), standard deviation of inverse DFT from trajectory curvature vector, difference between first and last terms in distribution of saccade following, difference between numbers of saccades with big and small following, first five components of FFT (derivative of distribution (log(fixation Duration))), and number of peaks (maximums) in re-fixation sequence, and position of first maximum in log(fix duration) histogram.

It is understood that while some of the determinations for features are appropriate for individual tests, others are more global and can be used across all tests. For example to determine percent looking time saccade features can be determined via mean of log(saccade length in coordinates), fixation features can be mean of log (fix duration), standard deviation of the log(fix duration), Gamma distribution fitting parameter a (log(fixDur)), Gamma distribution fitting parameter b (log(fixDur)), and First maximum in (1/log (fixation duration)) distribution, and heuristic features determined by standard deviation of derivative (inverse DFT distribution of saccade Following), first minimum in derivative of distribution (log(Square under saccade)), standard deviation of inverse DFT from trajectory curvature vector, difference between first and last terms in distribution of saccade following, difference between numbers of saccades with big and small following, first five components of FFT (derivative of distribution (log(fixation Duration))), and number of peaks (maximums) in re-fixation sequence.

Figure 4:
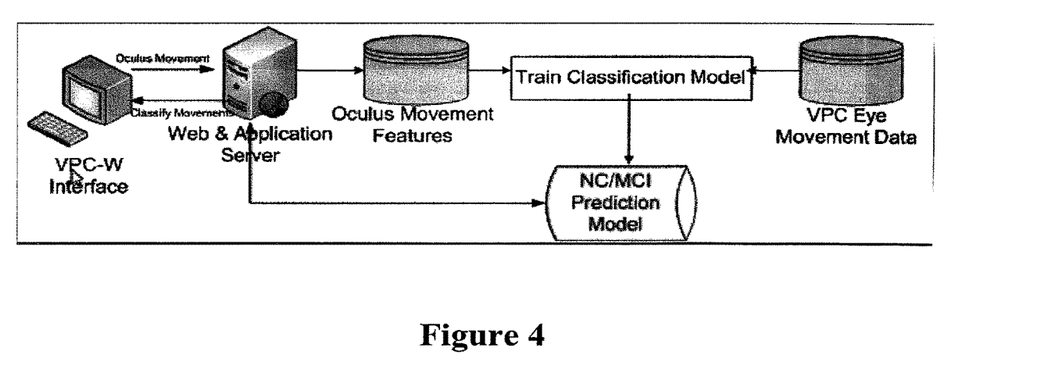
FIG. 4 shows the architecture of the visual comparison task as run on a computations device. The diagram shows the system components and the flow of information for training and examination of a subject.

It is understood that to create a diagnosis the features must be appropriately classified into normal and disease states which when combined can be used to create a diagnosis. Thus, in one aspect, disclosed herein are methods of training a machine learning system to classify features obtained while conducting a visual paired comparison test and translating the classified features into a diagnosis. It is understood that to create classifications data from known controls (normal and/or diseased subject) is measured and the optimal threshold to distinguish the normal controls from the diseased controls is determined. Robust features are determined by using one or more algorithms such as dispersion threshold based algorithms, velocity based algorithms, and area based algorithms. Once selected the robust features are used to create a classifier which is then used to accurately diagnose the disease state of a subject. It is understood that for each disease state, a different classifier is needed. For example, Alzheimer's disease has a different classifier than mild cognitive impairment, normal controls, and Parkinson's disease which in turn have different classifiers from each other and AD. Therefore, in one aspect, disclosed herein are methods of training a machine learning system to diagnose a cognitive disorder comprising obtaining data points (i.e., features) related to gaze position within an oculus for a subject with a known disease or non-disease state, determining the robust features using one or more algorithms, performing an analysis on the known samples to create a diagnosis, and comparing the determined diagnosis with actual disease state of the subject (see FIG. 4). It is understood that the training methods disclosed herein can further comprise a step of modifying the types of features or algorithms utilized to create a more accurate diagnosis.

Due to the potential for computational artifacts or noise, additional computations may be employed to reduce background noise such as the use of wavelet transform (e.g., Haar wavelet) over features. By applying the wavelet transform the prediction rate of the mouse tracking to distinguish normal controls from subjects with Alzheimer's disease, Parkinson's disease, or mild cognitive impairment can be raised to 100% accuracy. Similarly, one of skill in the art can apply these same techniques and algorithms to distinguish a subject with Alzheimer's disease from one with Parkinson's disease or MCI. Additionally, the test can distinguish a subject with MCI from a subject with Parkinson's disease. Therefore, it is further understood that the methods of disclosed herein (training or diagnosis) can further comprise a step which uses noise reduction In one aspect, disclosed herein are systems for assessing the presence of cognitive impairment in a subject comprising a computational device, a peripheral input device, and an image viewing device; wherein the subject uses visual image examination interface to observe novel and familiar images on the image viewing device and uses the peripheral input device to move an oculus over the images to slowly reveal parts of the image. It is understood and contemplated herein that as the oculus moves across the image, tracking/instrumentation data is collected and key features such as velocity, angle, trajectory, heuristic, fixation, and re-fixation are gathered. Based on the input, significant features are selected by computational device, classified based on established relationships and translated into a diagnosis utilizing selection algorithms. Thus, disclosed herein are systems for assessing the presence of cognitive impairment in a subject comprising a computational device, a peripheral input device, and an image viewing device; wherein the computational device comprises visual image examination interface and wherein the computational device takes data obtained from the input device and applies the data to a classifier; and wherein the data is then translated into a diagnosis (see FIG. 4).

A question arises whether the VPC task is sensitive specifically to medial temporal lobe damage in MCI or whether patients with other neurologic conditions, not specifically involving the medial temporal lobe, show impaired performance as well. In the present study, patients with PD as well as patients with MCI were assessed to address this question. PD is characterized by degeneration of dopaminergic neurons in the substantia nigra resulting in a depletion of dopamine. This depletion results in an abnormal motor behavior (e.g. resting tremor, rigidity, and akinesia) observed in this patient population (Lang A E, Lozano A M. N Engl J Med. 1998 Oct. 8; 339(15):1044-53); Lang A E, Lozano A M. N Engl J Med. 1998 Oct. 15; 339(16):1130-43). The cognitive profiles of PD patients can be heterogeneous and are frequently dominated by deficits in executive functioning (e.g. multi-tasking, planning, use of feedback) and visuospatial/visuoconstructional difficulties (Taylor A E, et al. Brain. 1986 October; 109 (Pt 5):845-83; Freeman R Q, et al. Neuropsychology. 2000 July; 14(3):415-26; Ong J C, et al. NeuroRehabilitation. 2005; 20(3):191-203). While memory impairment can occur in patients with PD (Whittington C J, et al. Neuropsychol. 2000 April; 14(2):233-46; Davidson P S, et al. Brain. 2006 July; 129(Pt 7):1768-79), these memory deficits are not attributed to an insidious disease process occurring in the medial temporal lobe. In the current study, recognition memory performance was unaffected by the presumed subcortical damage associated with the PD group, indicating that the VPC task is more selective to medial temporal lobe dysfunction (but see Whittington C J, et al. Neuropsychol. 2000 April; 14(2):233-46 for a meta-analysis of recognition impairment in Parkinson's Disease). These results support the use of the VPC task as an early diagnostic measure since it is sensitive to memory impairment.

Because patients with Parkinson's disease perform differently on the VPC task relative to subjects with MCI or AD, it is contemplated herein that the disclosed methods can be used to distinguish between Parkinson's Disease and MCI or AD. Thus disclosed herein are methods of determining whether cognitive loss in a subject is due to Parkinson's disease or mild cognitive impairment comprising conducting a visual paired-comparison test wherein the delay interval between the familiarization phase and the test phase is at least one minute, and wherein a decrease in looking time at the novel image relative to a normal control as determined by eye movement characteristics indicates the presence of mild cognitive impairment. Also disclosed are methods of determining whether cognitive loss in a subject is due to Parkinson's disease or mild cognitive impairment, wherein the MCI is early stage AD. Thus, also disclosed herein are methods of determining whether cognitive loss in a subject is due to Parkinson's disease or AD. Therefore, for example, disclosed herein are methods of determining whether cognitive loss in a subject is due to Parkinson's disease or MCI comprising conducting a visual paired-comparison test on a computer based system wherein the delay interval between the familiarization phase and the test phase is at least 10 seconds, wherein the eye movement characteristics for the subject are determined by measuring the movements of a peripheral input device for the computer, and wherein a decrease in looking time at the novel image relative to a normal control as determined by the eye movement characteristics indicates the presence of mild cognitive impairment. Also disclosed are methods of distinguishing Parkinson's disease from mild cognitive impairment in a subject comprising conducting a visual paired-comparison test on a computer based system wherein the delay interval between the familiarization phase and the test phase is at least 10 seconds, wherein the eye movement characteristics for the subject are determined by measuring the movements of a peripheral input device for the computer, and wherein a decrease in looking time at the novel image relative to a normal control as determined by eye movement characteristics indicates the presence of mild cognitive impairment.

It is understood that the disclosed methods of distinguishing Parkinson's disease from can be conducted from AD or MCI can be conducted on a computer based system or through the use of non-invasive eye tracking as disclosed herein. Thus, for example disclosed herein are in another aspect disclosed herein are methods of distinguishing Parkinson's disease from mild cognitive impairment in a subject or determining whether cognitive loss is due to Parkinson's disease or MCI comprising conducting a visual paired-comparison test wherein the delay interval between the familiarization phase and the test phase is at least one minute, and wherein a decrease in looking time at the novel image relative to a normal control as determined by eye movement characteristics indicates the presence of mild cognitive impairment. In a further aspect, disclosed herein are methods of distinguishing Parkinson's disease from mild cognitive impairment, wherein the MCI is early stage AD. Thus, also disclosed herein are methods of distinguishing Parkinson's disease from AD.

Additionally, it is understood that the disclosed diagnostic methods can also be used to rehabilitate memory impaired subjects by training the subjects to identify key features of an image to aid subsequent recognition. Thus, for example, the disclosed methods can be used to rehabilitate a subject with medial temporal damage such as hippocampal damage. Therefore, disclosed are methods of rehabilitating a subject with cognitive memory loss comprising administering to the subject a computer based visual paired-comparison test, measuring the movement of an input device throughout the test, comparing the subject's movement of the input device over an image for familiar image to the movements of a normal control for the same image, identifying uncommon fixations, and teaching the subject to increase fixations on areas of the familiar image where future recognition will result, and wherein the delay interval between the familiarization phase and the test phase is at least five seconds. Similarly, rehabilitation can occur through the use of non-invasive eye tracking used in conjunction with a visual paired comparison test. Therefore, disclosed are methods of rehabilitating a subject with cognitive memory loss comprising administering to the subject a visual paired-comparison test, assessing eye-tracking for the subject, comparing the eye-tracking of the subject for the familiar image to a normal control, identifying uncommon fixations, and teaching the subject to increase fixations on areas of the familiar image where future recognition will result, and wherein the delay interval between the familiarization phase and the test phase is at least 5 seconds. It is understood that the delay interval for rehabilitation can increase without affecting the accuracy of the results. For example the delay interval can be at least 5, 6, 7, 8, 9, 10, 11, 12, 13, 14, 15, 20, 25, 30, 35, 40, 45, 50, 55, or 60 seconds. The delay interval can also be at least 1.5, 2, 2.5, 3, 3.5, 4, 4.5, 5, 6, 7, 8, 9, or 10 minutes.

It is understood, that the disclosed methods can be assessed through the use of a device which possesses an input means by which cursor movement can be assessed. It is further understood that said device can be provided in a kit which includes a device for viewing the image, an input device, and a device to correlate the movements of the input device with gaze fixations. Thus, disclosed herein is a system for determining declarative memory loss in a subject comprising a image viewing device, an input device, and a computational device. It is understood that the image viewing device can be a computer monitor, the computation device can be a computer, and the input device can be a mouse.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1: Participants

Three subject groups were assessed. Group MCI: Six subjects diagnosed with mild cognitive impairment (mean age=70.0, SD=8.1); Group PD: Four subjects with Parkinson's Disease (mean age=63.8, SD=6.4); Group NC: Fifteen normal elderly control subjects (mean age=67.5, SD=5.6). All participants were recruited from the Alzheimer's Disease Research Center at Emory University, Atlanta, Ga. Informed consent was obtained for each participant in accordance with the regulations of the Institutional Review Board at Emory University.

A detailed medical, social and family history was obtained from each subject. MCI and PD patients had caregivers or informants who corroborated their history. Participants completed the five subtests of the Consortium to Establish a Registry for Alzheimer's Disease (CERAD) neuropsychological battery that included the following subtests: Animal naming, Boston Naming Test—15 item (BNT-15), Mini-Mental Status Exam (MMSE), Word List Memory (WLM) and Constructional Praxis (CP). Additional neuropsychological tests included Trail-Making Tests Parts A and B (TMT-A, TMT-B), Digit Span subtest of the Wechsler Adult Intelligence Scale—Revised (WAIS-R), and the Clock Drawing Test (Freedman M, et al. Clock drawing: A neuropsychological analysis. New York: Oxford University Press; 1994). The Geriatric Depression Scale (GDS) was administered to assess for the presence of depressive symptomatology. Group demographic information and neuropsychological performance for the three groups are summarized in Table 1. MCI and PD patients also received a full neurological examination. Clinical diagnoses of MCI, PD, or NC were established following a standardized assessment and review by three clinicians, expert in evaluation and management of Geriatric Neurology patients. Clinical diagnosis of MCI required evidence of a decline in baseline function in memory and additional cognitive domains, with the severity of symptoms or consequent functional limitations insufficient to meet DSM-III® criteria for Dementia. A diagnosis of PD was given if the participant fulfilled the criteria for PD according to the United Kingdom Parkinson's Disease Society Brain Bank clinical diagnostic criteria (Hughes A J, et al. J Neurol Neurosurg Psychiatry. 1992 March; 55(3):181-4). Participants were classified as NC if they demonstrated no evidence of cognitive decline from baseline functioning based on their clinical interview and assessment. Exclusion criteria included a history of substance abuse or learning disability, dementia, neurological (e.g. stroke, tumor) or psychiatric illness. Because the VPC task involves visual memory, subjects were also excluded if: 1) the eye tracking equipment did not achieve proper pupil and corneal reflection due to physiological constraints or visual problems (e.g. droopy eyelid, cataracts, detached retinas, glaucoma, pupils too small [7 subjects]); and/or 2) they did not complete the calibration procedure (3 subjects).

Example 2: Eye Tracking Equipment and Stimuli

During the task, participants' eye movements were continuously recorded using an Applied Science Laboratories (ASL) Model 5000 remote pan/tilt camera system. A ring of filtered near-infrared LEDs illuminated the eye and a high-speed, near-infrared sensitive CCD camera captured the pupil and corneal reflection. The gaze angle was determined by the relative positions of corneal and pupil centers with an accuracy of ±0.75°. The system sampled at 60 Hz, with a temporal resolution of 16 ms and linearity less than 10%. The participants were seated approximately 26 inches from a 19-inch flat panel computer screen that displayed the stimuli. No physical constraints other than a chinrest were used with the participants. Calibration for each subject was accomplished using a nine-point array. Eye fixation and eye movement data were recorded with ASL EYEPOS software. All images were black and white, high contrast clipart images measuring 4.4 inches wide by 6.5 inches high. Unique pictures were used for each trial.

Example 3: Procedure

Participants were brought into the testing room and seated comfortably in front of the monitor and their heads positioned within the chinrest to maintain their head/viewing position. Prior to presentation of the VPC task, a 9-point calibration procedure was completed. This was accomplished by having the subject fixate nine points at known locations on the computer monitor. The experimenter adjusted the calibration until the subject's fixations accurately mapped onto the calibration points on the screen. This calibration procedure enabled the eye tracking system to accurately compute the subject's gaze position on the computer monitor. Next, participants were informed that images would begin to appear on the computer monitor. They were simply instructed to look at the images "as if watching television." During the calibration and the test phase, the subjects' eye fixations and eye movements were recorded and stored for later analyses.

The entire testing procedure lasted approximately 25-30 minutes, including the calibration session. For the VPC task, subjects were administered four blocks of five trials (delay order: 2-minute delay, 2-second delay, 2-second delay, 2-minute delay) for a total of 20 trials. Each trial consisted of two phases; a familiarization phase followed by a test phase. During the familiarization phase, two identical pictures were presented side-by-side on the monitor for five seconds. The monitor then went dark for a delay interval of either two seconds or two minutes. Then, in the test phase, two pictures were again presented side-by-side for five seconds. One of the images was identical to the image presented during the familiarization phase and the other was a novel image. The side of presentation of the novel picture was selected pscudorandomly and it was presented equally often on the left or right side of the monitor screen. After the test phase of the trial, the monitor was darkened for 20 seconds until the beginning of the next trial. In order to ensure subject attention for test trials that had two-minute delays, the experimenter verbally alerted all subjects that there was "approximately ten seconds before the next pair of images."

Example 4: Data Analysis

Eye fixation and eye movement data for each participant were extracted and analyzed off-line using ASL EYENAL software. A fixation was defined as a point of gaze continually remaining within 1° of visual angle for a period of 100 msec or more. For the data analysis in the current study, the fixations analyzed occurred within two designated areas of interest (AOIs): the area of the novel image, and the area of the familiar image. Fixations outside the two areas were not included in the present analysis.

Eye tracking data were characterized using three measures: (1) total looking time (i.e. the total sum of the duration for all fixations); (2) total number of fixations (i.e. the total number of fixations that met the ≥100 msec criterion); and (3) percent looking time on novel image. For each measure, the median of the ten trials was calculated at each delay interval (2-sec, 2-min) for each subject. Finally, each measure was analyzed using a separate 3×2 repeated measures ANOVA, with group (MCI, PD, NC) as the between-subjects factor and delay (2-seconds, 2-minutes) as the within-subjects factor. All post-hoc pairwise comparisons were performed using the Tukey-Kramer test at $\alpha=0.05$ (two-tailed).

Example 5: Demographics and Global Cognitive Status

Analyses revealed there were no significant differences among the three subject groups in age, education, or global cognitive functioning as measured by several of the tests used by the CERAD, as well as the Trail Making Test, Digit Span, Clock Drawing, and the Geriatric depression Scale (all p's>0.05).). However, the MCI group was impaired on both the Word List Memory Total and the Word List Memory Delayed Recall measures compared to the NC group (p's<0.05. The MCI group was also impaired relative to both the NC (p<0.01) and PD (p<0.05) groups on a visuo-construction task as measured by the CP copy measure. On the delayed recall version of this task the MCI group performed worse than the PD group (p<0.05). No significant group differences in performance on any other neuropsychological measures were detected (all p's>0.05). Results are summarized in Table 1.

TABLE 1

| Group demographic information and neuropsychological performance scores | | | | |
|---|---|---|---|---|
| Measure | NC | MCI | PD | Tukey-Kramer * |
| Total N | 15 | 6 | 4 | |
| Age | 67.5 (5.6) | 70.0 (8.1) | 63.8 (6.4) | ns. |
| Education | 16.4 (2.3) | 16.3 (2.7) | 15.0 (2.6) | ns. |
| CERAD[a] | | | | |
| Animal Fluency | 20.9 (2.9) | 16.2 (5.6) | 17.0 (4.3) | ns. |
| Boston Naming Test -15 | 14.6 (.6) | 14.0 (.9) | 14.8 (.5) | ns. |
| Mini-Mental State Exam | 29.1 (1.3) | 27.5 (2.8) | 29.0 (.8) | ns. |
| Word List Memory (WLM) | | | | |
| WLM total | 24.0 (4.5) | 17.8 (1.9) | 21.0 (1.7) | NC vs MCI p < .01 |
| WLM delayed recall | 8.1 (1.8) | 5.2 (2.4) | 7.3 (.5) | NC vs MCI p < .01 |

TABLE 1-continued

Group demographic information and neuropsychological performance scores

| Measure | NC | MCI | PD | Tukey-Kramer * |
|---|---|---|---|---|
| Constructional Praxis (CP) | | | | |
| CP copy | 10.9 (.3) | 9.7 (1.5) | 11.0 (0) | NC vs MCI p <.01 |
|  |  |  |  | PD vs MCI p < .05 |
| CP delayed recall | 9.9 (2.1) | 7.2 (3.8) | 12.0 (1.4) | PD vs MCI p < .05 |
| Trail Making Test (TMT) | | | | |
| TMT- A | 33.6 (15.7) | 42.8 (16.1) | 36.7 (8.0) | ns |
| TMT- B | 74.8 (33.5) | 93.7 (14.9) | 59.3 (15.5) | ns |
| Digit Span Forwards | 11.1 (2.0) | 9.3 (2.2) | 13 (2.0) | ns |
| Digit Span Backwards | 8.1 (2.4) | 6.8 (1.3) | 7.0 (3.6) | ns |
| Clock Drawing Test | 12.7 (.6) | 12.7 (.5) | 12.0 (1.7) | ns |
| Geriatric Depression Scale | 2.4 (3.1) | 3.0 (1.7) | 2.7 (3.8) | ns |

Note:
The mean for each variable is given with SD in parentheses; ns. = ANOVA not significant,; no post-hoc tests were performed.
* If the ANOVA F was significant (p < .05), then the Tukey-Kramer post-hoc pair-wise comparisons were performed and p values are presented.
NC = normal control;
MCI = mild cognitively impaired;
PD = Parkinson's Disease
[a]Consortium to Establish a Registry for Alzheimer's Disease Example 6: Familiarization Phase: Total Looking Time and Total Number of Fixations During the familiarization phase, subjects were presented with two identical stimuli for 5 seconds prior to a 2-second or 2-minute delay. For total looking time (Table 2), the effects of group (F (2,22)=1.55, p=0.24), delay (F (1,22)=1.73, p=0.20) and group by delay interaction (F (2,22)=1.09, p=0.35) were nonsignificant, indicating that the three groups did not differ in the overall amount of time they spent looking at the familiarization images prior to either delay. Similarly, for the total number of fixations i.e., looking at either of the two identical stimuli, during the familiarization phase (Table 2), the effects of group (F (2,22)=1.26, p=0.30), delay (F (1,22)=0.04, p=0.85), and group by delay interaction (F (2,22)=0.22, p=0.80) were nonsignificant. These results indicate that all three groups made a similar number of fixations during the familiarization phase.

TABLE 2

Mean and standard deviations for total number of fixations and total looking time during the familiarization and test phases

| Eye tracking variables | NC | PD | MCI | Tukey-Kramer |
|---|---|---|---|---|
| Familiarization phase | | | | |
| Total number of fixations | | | | |
| 2-second delay | 10.53 (3.09) | 11.00 (1.15) | 8.83 (2.42) | ns |
| 2-minute delay | 10.77 (1.96) | 10.25 (1.71) | 9.00 (4.16) | ns |
| Total Looking Time (secs) | | | | |
| 2-second delay | 2.85 (1.05) | 3.37 (0.37) | 2.46 (0.78) | ns |
| 2-minute delay | 2.90 (0.54) | 2.76 (0.42) | 2.27 (0.99) | ns |
| Test phase | | | | |
| % Looking Time on Novel Stim. | | | | |
| 2-second delay | 71.39 (9.47) | 72.82 (10.50) | 76.06 (9.78) | ns |
| 2-minute delay | 73.75 (5.82) | 71.18 (6.10) | 52.71 (20.90) | * |
|  |  |  |  | NC vs MCI p < .01 |
|  |  |  |  | PD vs MCI p < .05 |
|  |  |  |  | NC vs PD ns |
| Total number of fixations | | | | |
| 2-second delay | 10.83 (2.93) | 10.50 (1.96) | 8.42 (3.97) | ns |
| 2-minute delay | 10.50 (2.60) | 10.00 (2.45) | 9.75 (2.54) | ns |
| Total Looking Time (secs) | | | | |
| 2-second delay | 3.03 (1.07) | 3.52 (0.52) | 2.24 (1.12) | ns |
| 2-minute delay | 3.06 (0.79) | 3.35 (0.42) | 2.58 (0.86) | ns |

Note:
The mean for each variable is given with standard deviations in parentheses
NC = normal control;
MCI = mild cognitive impairment;
PD = Parkinson's Disease
* = Tukey-Kramer post-hoc comparisons revealed significant differences between MCI and PD (p < .047), and MCI and NC (p < .002). No significant differences were detected between NC and PD (p = .85); ns = nonsignificant.

Example 7: Test Phase: Percent Time Looking at the Novel Image

During the test phase, subjects were presented with the original image from the familiarization phase together with a novel image for 5 seconds. The percent time looking at the novel image was the main measure of interest. There was a significant group by delay interaction (F (2,22)=5.39, p=0.012). For the 2-second delay, all three groups spent similar amounts of time looking at the novel image (71-76%; F (2,22)=0.50, p=0.61); Table 2. However, for the 2-minute delay, the groups differed in their percent time looking at the novel stimulus (F (2,22)=7.69, p=0.003). Specifically, the MCI group spent only 53% of their total looking time viewing the novel image, compared to the PD group (71%) and the NC group (74%) (p's<0.05). The PD and NC groups did not differ from one another (p=0.91).

Additional analyses revealed that impaired performance of the MCI group at the 2-minute delay was not due to group differences in the overall time spent looking at the images or group differences in the overall number of fixations on the images. For total number of fixations (Table 2), the effects of group (F (2,22)=0.81, p=0.46), delay (F (1,22)=0.09, p=0.77) and group by delay interaction (F (2,22)=1.12, p=0.34) were nonsignificant. This demonstrates that all three groups made similar numbers of fixations during the test phase. Furthermore, for total looking time the effects of group (F (2,22)=2.03, p=0.16), delay (F (1,22)=0.16, p=0.69), and group by delay interaction (F (2,22)=0.72, p=0.50) were also nonsignificant. Therefore, groups did not differ in the amount of overall time spent looking at images during the test phase.

Example 8: The VPC Task can Detect Mild Cognitive Impairment in Humans

This work has demonstrated that patients diagnosed with MCI display impaired recognition memory performance compared to NC and PD groups. Specifically, all three groups demonstrated equivalent recognition memory performance (characterized by increased viewing time of the novel image relative to the familiar image) at the 2-sec delay. However, the MCI group showed a significant reduction in the amount of time they spent looking at the novel image when the delay interval was increased to two minutes. At the 2-min delay, NC and PD groups spent 74% and 71% (respectively) of the total looking time viewing the novel stimulus; inversely, they viewed the familiar image only 26-29% of the total looking time. By contrast, the MCI group spent only 53% of the total looking time viewing the novel stimulus, and approximately 47% of the total looking time viewing the familiar stimulus. Thus, the MCI group spent about equal amounts of time looking at both the novel and familiar images. These results indicate that the delay interval of 2 minutes sufficiently challenged the memory system so that the MCI subjects no longer remembered which image they had previously seen. Thus, the VPC task can successfully detect MCI in humans.

Example 9: Performance on the VPC Task is Sensitive Specifically to Hippocampal Damage The MCI group did not meet DSM-III criteria for dementia (Table 1). Instead, the MCI group evidenced a decline in memory function as measured by some of the tasks described in Table 1, and in particular by their selective deficit in performance on the 2-min delay portion of the VPC task, but not on the 2-sec delay portion of the task (the relevance of findings with the 2-sec delay is discussed below). Thus, one can ask whether there is evidence that links MCI impairment to disruption limited to the brain's memory systems, e.g., the medial temporal lobe (MTL) memory system (Squire L R, Zola-Morgan S. Science. 1991 Sep. 20; 253(5026):1380-6), and the hippocampus in particular. There are cumulating data from work with animals as well as with humans indicating that the impairment in the MCI group reported here is linked to hippo campal dysfunction. Specifically, the observed performance on the VPC task by the MCI group closely resembles performance on a similar VPC task administered to nonhuman primates who sustained lesions limited to the hippocampus (Zola S M, et al. J Neurosci. 2000 Jan. 1; 20(1):451-63). The monkeys with hippocampal lesions had a reduction in looking time at the novel stimulus as the delay interval on the VPC task was increased from 1 sec to 10 min. These monkeys had lesions of the hippocampus made by radiofrequency or by ibotenic acid. Similar to the MCI patients in the present study, monkeys with either RF or IBO lesions spent more time viewing the novel image on the VPC task when the delay interval was short (1 sec), with less time viewing the novel image as the delay interval increased. A similar pattern has also been observed in rats with hippocampal lesions (Clark R E, et al. J Neurosci. 2000 Dec. 1; 20(23):8853-60). Other studies using memory impaired patients with damage limited to the hippocampus and similar tasks of recognition memory have also pointed to the importance of intact hippocampal function for successful performance (Smith, C N, et al. J Neurosci. 2006 Nov. 1; 26(44):11304-11312). Thus, findings from work in humans, as well as monkeys, and rats all provide converging evidence that impairment on the VPC task reflects memory problems associated with hippocampal dysfunction.

At the time of the present study, only one of the six MCI subjects had undergone magnetic resonance imaging (MRI) scanning. This patient was impaired in all of the tasks that the MCI group was impaired on in Table 1. Additionally, this patient's performance on the VPC task was 62% at the 2-min delay, a score that was worse than all but one control subject. In the MCI subject, an MRI examination without gadolinium was performed according to a standard department (Neurology) protocol on a 3T magnet (Siemens Magneton Trio). Axial gradient-echo images for susceptibility were also performed. The clinical report, based on reviews of the images, indicated scattered foci of T2 prolongation in the periventricular and subcortical white matter of both hemispheres. Additionally, slight prominence of the sulci, cisterns, and ventricles, consistent with mild diffuse volume loss was noted. There was no evidence of acute territorial infarction, hemorrhage, mass, mass-effect or midline shift. The major intracranial vascular flow-voids also were reported as intact. Importantly, there was no reported evidence of abnormalities in the hippocampal region or in adjacent cortical regions of the medial temporal lobe. The MRI findings from this case indicate that impaired performance on the VPC task by patients with MCI precedes detectable structural changes in the hippocampus and the medial temporal lobe region. Therefore, sensitive behavioral tasks like the VPC task combined with infrared eye tracking can serve as predictive biomarkers for underlying but as yet undetectable brain pathology or regional brain dysfunction, e.g., vascular subcortical pathology.

Example 10: The Impaired Performance Exhibited by the MCI Group on the VPC Task is not Attributable to Aspects of Performance Other than Memory It is possible that the differences in performance between the MCI and the NC groups on the 2-min delay portion of the VPC task occurs for reasons other than memory impairment on the part of the MCI group. Several possibilities include differences between the MCI and the NC groups in global cognitive status and demographics, or differences in attentional, motivational, and perceptual functions. However, as shown in Table 1, the groups were equivalent on cognitive status, age and education. Nor can the results be explained by group differences in attentional, motivational, or perceptual abilities since all groups performed equivalently at the 2-sec delay. Analyses revealed that all three groups were equivalent in the total amount of time they viewed the pictures during either phase, indicating all three groups were similarly able to attend to and accurately perceive the stimuli. Additionally, the number of fixations that met criteria for analyses cannot account for the observed group differences because the number of fixations that met criteria was not different for any group. Thus, the two groups performed quite similarly in all important ways that provided evidence for a competing suggestion to that of impaired memory in the MCI group. Accordingly, the idea that the MCI group's impaired performance on the 2-min delay portion of the task resulted from impaired memory remains compelling.

As used in the present study, eyetracking provided objective and quantitative evidence of each subject's visual, attentional, and memory processes. Moreover, the eye movement data were acquired in an unobtrusive, noninvasive manner and provided on-line measures as well as data-based storage of information for later analyses. Additionally, eyetracking allowed for a number of potentially informative and sensitive measures in addition to a simple novel stimulus viewing-time measure. Thus, two additional parameters were measured, i.e., overall viewing time, and number of fixations, helped to eliminate the possibility that the impaired performance by the MCI group was attributed to factors other than mnemonic dysfunction.

Example 11: Web-Based VPC Task Design and Optimization

Figure 1:
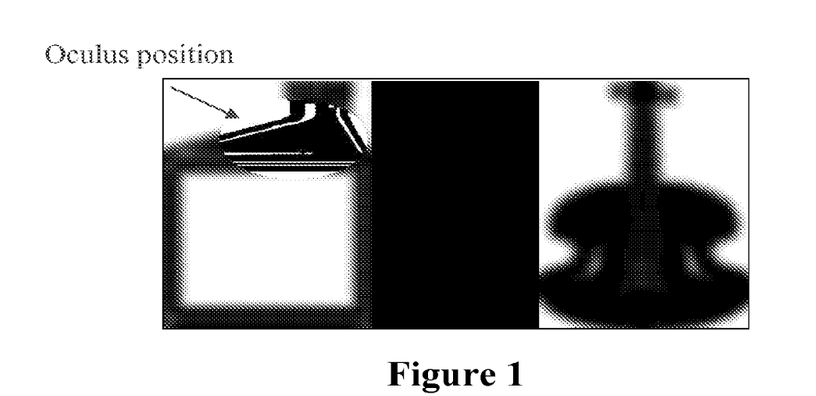
FIG. 1 shows an illustration of Web VPC task viewing familiar and novel images (blurred), with an oval-shaped oculus.

The software methodology disclosed herein imitates the eye-tracker-based VPC task using internet-enabled computers. One implementation version, VPC-w, uses an oval-shaped "oculus" to incrementally reveal images to the subject, while blurring the rest of the image using a low-pass filter. The oculus can be moved through the picture using a computer mouse or touch pad. A snapshot of VPC-w in operation is illustrated in FIG. 1, where the oculus is currently positioned over the left image.

In order to reduce VPC-w to practice, the setting of the implementation needed to be adapted to mirror eye tracking data. Making the setting modifications of the VPC-w implementation required months of experimentation with hundreds of normal control subjects recruited over the internet. Specifically, the use of and the size of the oculus; the length of the familiarization and the test stages, the amount of blur, and the order and the set of the images were varied. The goal was to maximize the average preference for the novel image, for all NC subjects. An example of the VPC-w settings which mirrored the eye tracking data are reported in Table 3.

TABLE 3

VPC-w settings optimized by maximizing novel preference for Normal Control (NC) subjects

| Parameter Name | Value | Description and Comments |
| --- | --- | --- |
| Stage time | 10 seconds | Time used to present the familiar image pair in the familiarization stage and the pair of (familiar image, novel image) in the test stage. |
| Oculus size | (180, 120) | Oval with 180 width 120 height |
| Blur amount | (3, 20) | 3 loops of blur (low-pass Gaussian filter) with radius 20 pixels |
| Image set | (3, 7) | First 3 image pairs are used for training; Last 7 image pairs are selected to be unbiased by switching the novel and familiar images. |

Figure 2:
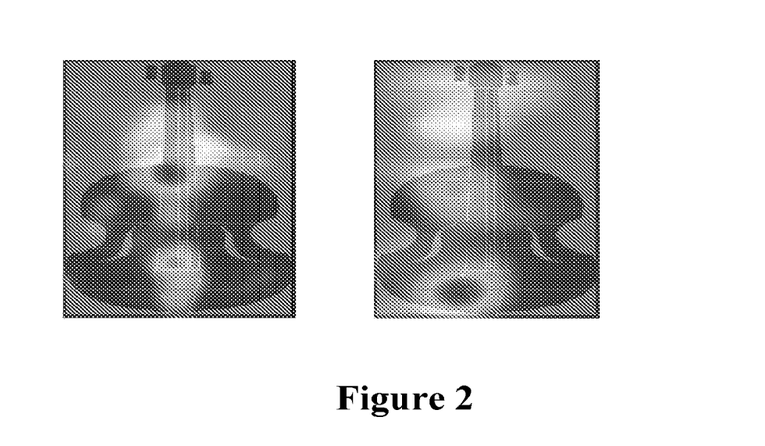
FIG. 2 shows the viewing behavior of a novel image using eye tracking (left) and VPC-w (right) for normal control (NC) subjects.

Example viewing behavior for eye tracking-based and VPC-w with these settings is shown in FIG. 2. The viewing is represented using intensity "heat maps", where the color represents the overall time spent looking at the corresponding region of the image. While the viewing behavior using VPC-w differs from eye-tracking performance, there are encouraging similarities in the regions of attention. For example, while using VPC-w is more "noisy" and diverse, the differences of the viewing behavior between normal controls and impaired subjects can be captured with the machine learning techniques developed for both eye movement analysis and mouse movement analysis.

Example 12: Machine Learning for High-Accuracy Subject Categorization

Machine learning techniques are widely used in computer science and medicine for classification of data patterns. A machine learning-based methodology for classification of healthy subjects and patients with Alzheimer disease was developed based on a novel representation of the eye movement data. This analysis involves a characterization of the speed and trajectory of gaze movements including fixation position, duration and distribution, saccade length, re-fixations, saccade angles and many others. The resulting features are further processed using wavelet transformation and other digital signal processing techniques to reduce noise and improve classification accuracy. Preliminary experimental results exhibited accuracy over 95% in classifying control subjects vs. Alzheimer's patients based on patterns of eye movement. This represents a significant improvement over existing methods. The same analysis techniques can be applied to automatically classify subjects using the Web-based VPC task.

Example 13: Validation Results of VPC-w Performance (Normal Control Subjects)

The validation results disclosed herein show that VPC-w induces image viewing behavior in Normal Control (NC) subjects that is comparable to that of eye tracking-based viewing (Table 4). The preference for viewing novel images is nearly 59% for 10 second delay, and approximately 58% for 60 second delay between familiarization and test stages. The preference for novel image vs. chance is significant (unpaired t-test, p<0.001). If outliers on either side of the mean are removed, the overall results do not change, with 10-second delay exhibiting higher preference than for the 60-second delay, with lower dispersion. In comparison, novelty preference in normal subjects using eye tracking, with comparable delays between familiarization and test stages is about 70%.

TABLE 4

Novel Image Preference for varying delay times with optimized VPC-w settings. Novel preference values are significant with $p < 0.001$

| Delay (seconds) | All Subjects | | Outliers Removed | |
| --- | --- | --- | --- | --- |
| | N | Novel Pref. (%) and 5-95% Conf. Interval | N | Novel Pref. (%) and 5-95% Conf. Interval |
| 10 | 47 | 58.8*** [0.47, 0.77] | 37 | 58.4*** [51.2, 66.9] |
| 60 | 60 | 57.8*** [46.0, 73.9] | 37 | 55.7** [49.4, 65.2] |

Example 14: Principal Component Analysis

Figure 3:
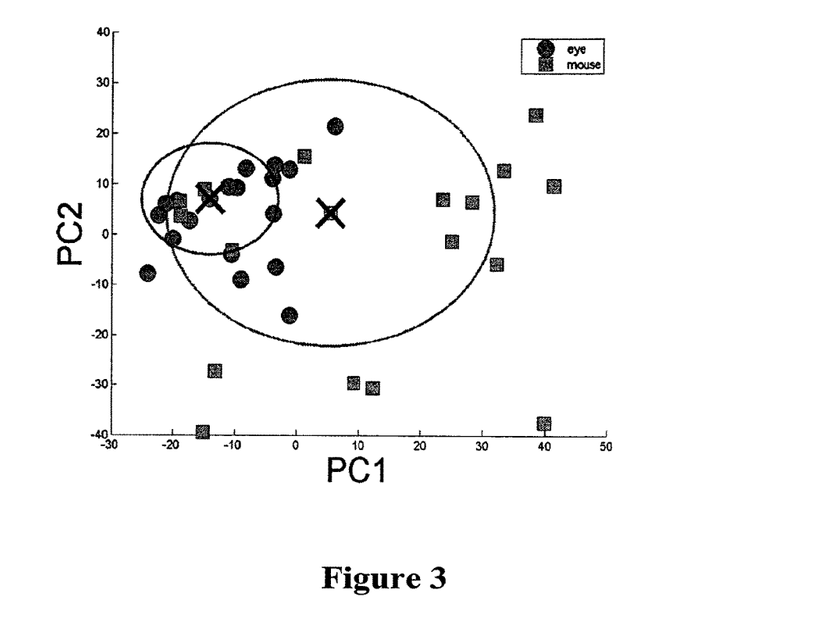
FIG. 3: shows eye tracking-based data (N=20, "eye" points) and VPC-w data (N=20, "mouse" points) for a sample of subjects' viewing of the example novel image FIG. 2, projected into the first two PCA dimensions PC1 and PC2.

In order to better understand the similarity between eye tracking-based and VPC-w heatmaps, principle component analysis (PCA) decompositions were computed of the heatmaps of the eye tracking-based and VPC-w data. FIG. 3 depicts subjects' data in the coordinate system of the first two (most important) principal components. A subject nearest to the centroid of each group was chosen as a representative point in PCA space for each group; the radius of corresponding circles indicates the mean Euclidian distance between group representative and its members. While the eye tracking data and VPC-w data in PCA space appear dispersed, the representatives of the groups are relatively close, indicating that there is some correspondence between the viewing heatmaps.

A. REFERENCES

Bachevalier J, Brickson M, Hagger C. Limbic-dependent recognition memory in monkeys develops early in infancy. *Neuroreport.* 1993 January; 4(1):77-80.

Berlyne D E. *Conflict, arousal, and curiosity.* New York: McGraw-Hill; 1960.

Braak H, Braak E. Diagnostic criteria for neuropathologic assessment of Alzheimer's disease. *Neurobiol Aging.* 1997 July-August; 18(4 Suppl):S85-8.

Braak H, Braak E. Neuropathological stageing of Alzheimer-related changes. *Acta Neuropathol (Berl).* 1991; 82(4):239-59.

Burns A, Zaudig M. Mild cognitive impairment in older people. *Lancet.* 2002 Dec. 14; 360(9349):1963-5.

Clark R E, Zola S M, Squire L R. Impaired recognition memory in rats after damage to the hippocampus. *J Neurosci.* 2000 Dec. 1; 20(23):8853-60.

Crutcher, Michael D.; Calhoun-Haney, Rose; Manzanares, Cecelia M.; Lah, James J.; Levey, Allan I.; and Zola, Stuart (2009) Eye Tracking During a Visual Paired Comparison Task as a Predictor of Early Dementia; *American Journal of Alzheimer's Disease and Other Dementias* Vol. 24, No. 3, P. 258.

Daffner K R, Mesulam M M, Cohen L G, Scinto L F. Mechanisms underlying diminished novelty-seeking behavior in patients with probable Alzheimer's disease. *Neuropsychiatry Neuropsychol Behav Neurol.* 1999 January; 12(1):58-66.

Daffner K R, Scinto L F, Weintraub S, Guinessey J E, Mesulam M M. Diminished curiosity in patients with probable Alzheimer's disease as measured by exploratory eye movements. *Neurology.* 1992 February; 42(2):320-8.

Davidson P S, Anaki D, Saint-Cyr J A, Chow T W, Moscovitch M. Exploring the recognition memory deficit in Parkinson's disease: estimates of recollection versus familiarity. *Brain.* 2006 July; 129(Pt 7):1768-79.

Eichenbaum H. The hippocampus and declarative memory: cognitive mechanisms and neural codes. *Behav Brain Res.* 2001 Dec. 14; 127(1-2):199-207.

Elias M F, Beiser A, Wolf P A, Au R, White R F, D'Agostino R B. The preclinical phase of alzheimer disease: A 22-year prospective study of the Framingham Cohort. *Arch Neurol.* 2000 June; 57(6):808-13.

Fagan J F, 3rd. Memory in the infant. *J Exp Child Psychol.* 1970 April; 9(2):217-26.

Fagan J F, 3rd. The paired-comparison paradigm and infant intelligence. *Ann N Y Acad Sci.* 1990; 608:337-57; discussion 58-64.

Freedman M, Leach L, Kaplan E, Winocur G, Shulman K, Delis D. *Clock drawing: A neuropsychological analysis.* New York: Oxford University Press; 1994.

Freeman R Q, Giovannetti T, Lamar M, Cloud B S, Stern R A, Kaplan E, et al. Visuoconstructional problems in dementia: contribution of executive systems functions. *Neuropsychology.* 2000 July; 14(3):415-26.

Giacobini E. Cholinesterase inhibitors stabilize Alzheimer's disease. *Ann N Y Acad Sci.* 2000; 920:321-7.

Hughes A J, Daniel S E, Kilford L, Lees A J. Accuracy of clinical diagnosis of idiopathic Parkinson's disease: a clinico-pathological study of 100 cases. *J Neurol Neurosurg Psychiatry.* 1992 March; 55(3):181-4.

Lang A E, Lozano A M. Parkinson's disease. First of two parts. *N Engl J Med.* 1998 Oct. 8; 339(15):1044-53.

Lang A E, Lozano A M. Parkinson's disease. Second of two parts. *N Engl J Med.* 1998 Oct. 15; 339(16):1130-43.

Linn R T, Wolf P A, Bachman D L, et al. The 'preclinical phase' of probable Alzheimer's disease. A 13-year prospective study of the Framingham cohort. *Arch Neurol.* 1995 May; 52(5):485-90.

Loftus G R, Mackworth N H. Cognitive determinants of fixation location during picture viewing. *J Exp Psychol Hum Percept Perform.* 1978 November; 4(4):565-72.

Manns J R, Stark C E, Squire L R. The visual paired-comparison task as a measure of declarative memory. *Proc Natl Acad Sci USA.* 2000 Oct. 24; 97(22):12375-9.

McKee R D, Squire L R. On the development of declarative memory. *J Exp Psychol Learn Mem Cogn.* 1993 March; 19(2):397-404.

Morris J C. Mild cognitive impairment and preclinical Alzheimer's disease. *Geriatrics.* 2005 June; Suppl:9-14.

Mosimann U P, Muri R M, Burn D J, Felblinger J, O'Brien J T, McKeith I G. Saccadic eye movement changes in Parkinson's disease dementia and dementia with Lewy bodies. *Brain.* 2005 June; 128(Pt 6):1267-76.

Ong J C, Seel R T, Came W F, Brown R, Pcgg P O, Jchlc P J. A brief neuropsychological protocol for assessing patients with Parkinson's disease. *NeuroRehabilitation.* 2005; 20(3): 191-203.

Petersen R C, Smith G E, Waring S C, Ivnik R J, Tangalos E G, Kokmen E. Mild cognitive impairment: clinical characterization and outcome. *Arch Neurol.* 1999 March; 56(3):303-8.

Petersen R C, Stevens J C, Ganguli M, Tangalos E G, Cummings J L, DeKosky S T. Practice parameter: early detection of dementia: mild cognitive impairment (an evidence-based review). Report of the Quality Standards Subcommittee of the American Academy of Neurology. *Neurology.* 2001 May 8; 56(9):1133-42.

Q. Guo and E. Agichtein (2008) Exploring Client-Side Instrumentation for Personalized Search Intent Inference: Preliminary Experiments, *Proc. of the AAAI* 2008 *Workshop on Intelligent Techniques for Web Personalization and Recommender Systems* (*ITWP*).

Q. Guo, E. Agichtein (2008) Exploring Mouse Movements for Inferring Query Intent; *Proc. of the ACM SIGIR International Conference on Research and Development in Information Retrieval.*

Q. Guo, E. Agichtein, C. Clarke and A. Ashkan (2009) In the Mood to Click? Towards Inferring Searcher Receptiveness to Search Advertising; *Proc. of the ACM/IEEE Web Intelligence Conference.*

Richmond J, Sowerby P, Colombo M, Hayne H. The effect of familiarization time, retention interval, and context change on adults' performance in the visual paired-comparison task. *Dev Psychobiol.* 2004 March; 44(2): 146-55.

Schenk D, Barbour R, Dunn W, et al. Immunization with amyloid-beta attenuates Alzheimer-disease-like pathology in the PDAPP mouse. *Nature.* 1999 Jul. 8; 400(6740): 173-7.

Smith, C N, Hopkins, R O, Squire, L R. Experience-dependent eye movements, awareness, and hippocampus-dependent memory. J Neurosci. 2006 Nov. 1; 26(44): 11304-11312.

Squire L R, Zola-Morgan S. The medial temporal lobe memory system. *Science.* 1991 Sep. 20; 253(5026):1380-6.

Taylor A E, Saint-Cyr J A, Lang A E. Frontal lobe dysfunction in Parkinson's disease. The cortical focus of neostriatal outflow. *Brain.* 1986 October; 109 (Pt 5):845-83.

Whittington C J, Podd J, Kan M M. Recognition memory impairment in Parkinson's disease: power and meta-analyses. *Neuropsychol.* 2000 April; 14(2):233-46.

Zola S M, Squire L R, Teng E, Stefanacci L, Buffalo E A, Clark R E. Impaired recognition memory in monkeys after damage limited to the hippocampal region. *J Neurosci.* 2000 Jan. 1; 20(1):451-63.

What is claimed is:

1. A method of diagnosing cognitive impairment of a subject, comprising
   conducting a visual paired-comparison (VPC) test on a computer based system, the VPC test including one or more trials, each trial simultaneously displaying areas of interest of a novel image to a subject and displaying areas of interest in a familiar image to both eyes the subject;
   receiving in an application server eye movement characteristics for the subject for each trial from the computer based system during the VPC test by the subject, wherein the eye movement characteristics are associated with the areas of interest of the novel image and the areas of interest of the familiar image;
   detecting in the application server whether the eye movement characteristics for the subject match at least one classifier, wherein the one classifier is associated with the cognitive impairment.

2. The method of claim 1, wherein the areas of interest of the novel image and the areas of interest of the familiar image are not blurred.

3. The method of claim 1, wherein the cognitive impairment is selected from a group consisting of Parkinson's Disease, mild cognitive impairment, cognitive decline, and Alzheimer's Disease.

4. The method of claim 2, wherein the novel image comprises portions that are blurred to the subject and the areas of interest of the novel image that are not blurred to the subject.

5. The method of claim 1 further comprising
   receiving on the computer based system movements of a peripheral input device by the subject;
   displaying to the subject on the computer based system an area of interest of the novel image in response to the movements of the peripheral input device.

6. The method of claim 5, wherein the peripheral input device is selected from the group consisting of a mouse, touchpad, a joystick, a trackball, a light pen, and a touch screen.

7. The method of claim 1 further comprising
   determining in the application server rehabilitation steps for the subject in response to the cognitive impairment; and
   providing the subject with the rehabilitation steps.

8. The method of claim 7, wherein the rehabilitation steps comprise training the subject to identify a feature of a familiar image.

9. The method of claim 7, wherein the rehabilitation steps comprise teaching the subject to increase fixation on one or more areas of the familiar image to facilitate recognition.

10. A system for diagnosing cognitive impairment of a subject, comprising
    a computer based system for conducting a visual paired-comparison (VPC) test, the VPC test including one or more trials, wherein each trial simultaneously displays areas of interest of a novel image to a subject and displays areas of interest in a familiar image to both eyes of the subject; and
    an application server coupled to the computer based system for receiving eye movement characteristics for the subject for each trial from the computer based system during the VPC test by the subject, wherein the eye movement characteristics are associated with the areas of interest of the novel image and the areas of interest of the familiar image, and for detecting whether the eye movement characteristics for the subject match at least one classifier, wherein the one classifier is associated with the cognitive impairment.

11. The system of claim 10, wherein the areas of interest of the novel image and the areas of interest of the familiar image are not blurred.

12. The system of claim 10, wherein the cognitive impairment is selected from a group consisting of Parkinson's Disease, mild cognitive impairment, cognitive decline, and Alzheimer's Disease.

13. The system of claim 11, wherein the novel image comprises portions that are blurred to the subject and the areas of interest of the novel image that are not blurred to the subject.

14. The system of claim 10, wherein the computer based system is for receiving on the computer based system movements of a peripheral input device by the subject, and for displaying to the subject on the computer based system an area of interest of the novel image in response to the movements of the peripheral input device.

15. The system of claim 14, wherein the peripheral input device is selected from the group consisting of a mouse, touchpad, a joystick, a trackball, a light pen, and a touch screen.

16. The system of claim 10, wherein the application server is for determining in the application server rehabilitation steps for the subject in response to the cognitive impairment, and for providing the subject with the rehabilitation steps.

17. The system of claim 16, wherein the rehabilitation steps comprise training the subject to identify a feature of a familiar image.

18. The system of claim 17, wherein the rehabilitation steps comprise teaching the subject to increase fixation on one or more areas of the familiar image to facilitate recognition.

* * * * *